(12) United States Patent
Inoue et al.

(10) Patent No.: US 6,456,873 B1
(45) Date of Patent: Sep. 24, 2002

(54) BODY FAT METER

(75) Inventors: Hiroyoshi Inoue, Miki; Yasutoshi Masuda, Akashi, both of (JP)

(73) Assignee: Yamato Scale Co., Ltd., Hyogo (JP)

( * ) Notice: Subject to any disclaimer, the term of this patent is extended or adjusted under 35 U.S.C. 154(b) by 0 days.

(21) Appl. No.: 09/509,056

(22) PCT Filed: Jul. 19, 1999

(86) PCT No.: PCT/JP99/03884

§ 371 (c)(1),
(2), (4) Date: May 8, 2000

(87) PCT Pub. No.: WO00/04826

PCT Pub. Date: Feb. 3, 2000

(30) Foreign Application Priority Data

Jul. 23, 1998 (JP) ............................. 10-207641

(51) Int. Cl.[7] ................................. A61B 5/05
(52) U.S. Cl. ................... 600/547; 128/734; 128/897
(58) Field of Search .................. 600/547; 128/897, 128/734

(56) References Cited

U.S. PATENT DOCUMENTS 5,372,141 A * 12/1994 Gallup et al. ............... 128/734
5,415,176 A *  5/1995 Sato et al. .................. 128/734

FOREIGN PATENT DOCUMENTS

| JP | 60-156436 | 8/1985 |
| JP | 1-119614 | 8/1989 |
| JP | 5-2164 | 1/1993 |
| JP | 7-108039 | 4/1995 |
| JP | 2773706 | 4/1998 |
| JP | 10-174679 | 6/1998 |
| JP | 10-179535 | 7/1998 |

* cited by examiner

*Primary Examiner*—Marvin M. Lateef
*Assistant Examiner*—Devaang Shah
(74) *Attorney, Agent, or Firm*—Marshall, Gerstein & Borun

(57) ABSTRACT

A first current path forming electrode, a first measuring electrode, a second current path forming electrode and a second measuring electrode which serve to measure an impedance of a human body of a subject for a body fat ratio are formed on an electronic circuit board.

11 Claims, 5 Drawing Sheets

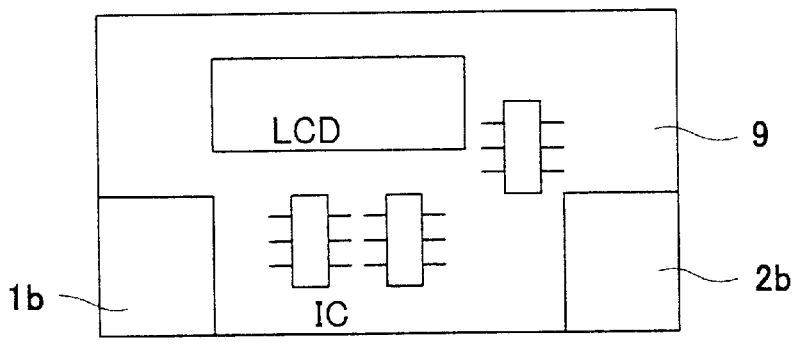
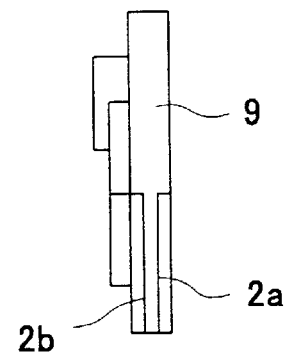
FIG. 3A    FIG. 3B
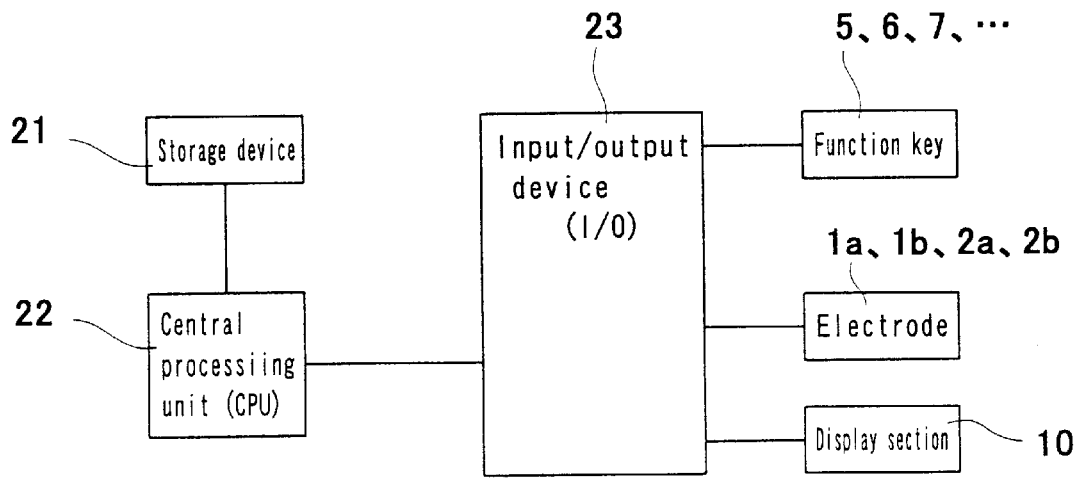
FIG. 4

BODY FAT METER

TECHNICAL FIELD

The present invention relates to a body fat determining device which can be small-sized.

BACKGROUND ART

Conventionally, attention has been given to a body fat ratio as the standard of a fat amount in a body in respect of maintenance of health, and a body fat ratio has been measured in order to prevent adult diseases and the like. Examples of a device for measuring such a body fat ratio include a body fat determining device. The body fat determining device has the following schematic structure.

The body fat determining device is provided with four electrodes for measuring an impedance of a human body of a subject. More specifically, a pair of current path forming electrodes for forming a current path between two points of a body by flowing a constant current and a pair of measuring electrodes for measuring a voltage between two points in the formed current path are provided such that the impedance of the human body can be detected by a contact of the hands of the subject and the like.

Moreover, the body fat determining device comprises an operation switch necessary for inputting individual data such as a height of the subject, a weight thereof and the like, a display unit for displaying these data, and a circuit element such as a CPU for performing an operation to calculate a body fat ratio from the impedance of the human body and the individual data.

The circuit element and the four electrodes (which will be hereinafter referred to as an "electrode group") are connected as a circuit such that the impedance of the human body measured through the electrodes can be processed as data for calculating a body fat ratio, and can be caused to function as a body fat determining device.

As an example of a conventional body fat determining device, circuit elements other than the electrode group are mounted and collected into an electronic circuit board such as a printed board and each electrode of the electrode group is provided as a separate member which is physically independent of the electronic circuit board. In such a body fat determining device, each electrode and other circuit elements have been connected through a wiring such as a cable to be connected to necessary portions of the electronic circuit board.

Accordingly, it has been required that such a body fat determining device is provided with the electrode group as an independent member in addition to the electronic circuit board on which various circuit elements for functioning as the body fat determining device are mounted. For this reason, a space for providing such an electrode group should be required, and furthermore, a wiring for connecting the electrode group to other circuit elements, a support table for supporting the electrode group on the body fat determining device and the like should be provided. In order to perform a work for manufacturing the body fat determining device, moreover, a large number of members should be provided, and furthermore, it has been necessary to take a working man-hour for connecting the electrode group to other circuit elements through a wiring. Consequently, the manufacturing cost of the body fat determining device has also been increased.

It is an object of the present invention to provide a body fat determining device which can reduce a space required for members constituting the body fat determining device to be small-sized and can reduce a working man-hour and manufacturing cost for manufacture.

DISCLOSURE OF THE INVENTION

The present invention provides a body fat determining device comprising an electrode group including a first current path forming electrode and a second current path forming electrode for forming a current path together with the first current path forming electrode, and a first measuring electrode and a second measuring electrode for measuring an impedance together with the first measuring electrode, and an electronic circuit board on which a circuit element is provided and a body case, wherein the electrode included in the electrode group is formed on the electronic circuit board, and the electrode group is formed with a face with which a subject comes in contact exposed to an outside of the body case in such a manner that the subject can come in contact to measure his (her) impedance.

According to the body fat determining device, it is not necessary to provide the electrode as a physically independent member on the electronic circuit board. More specifically, the electronic circuit generally includes a conductor portion for forming a circuit pattern and an insulating material portion. By scraping off the insulating material covering the conductor portion to expose the conductor portion to the outside in a portion of the electronic circuit board where the electrode group is to be formed, the conductor portion thus exposed is formed as the electrode on the electronic circuit board.

Consequently, the space for providing the electrode is eliminated. Moreover, it is not necessary to use a wiring for connecting the electrode to other circuit elements, a support table for supporting the electrode on the body fat determining device and the like. Consequently, the body fat determining device can be small-sized. Thus, the working man-hour can also be reduced for the manufacture of the body fat determining device, and furthermore, the manufacturing cost can be cut down.

In particular, in the case where the electronic circuit board on which the electrode is formed is provided with a circuit element constituting the body fat determining device, the size of the body fat determining device can be reduced still more and the number of members can also be decreased.

Moreover, in the case where the electronic circuit board on which the electrode is formed and another electronic circuit board on which circuit elements constituting the body fat determining device other than the electrode formed on the electronic circuit board are provided have a multi stage structure, it is possible to provide a necessary circuit element in the space between the electronic circuit board and the another electronic circuit board. Consequently, in the case where the body fat determining device cannot be increased in a transverse direction along the face of the electronic circuit board on which the element is to be provided, the necessary element can be provided by effectively utilizing the space in the vertical direction in which the electronic circuit board and the another electronic circuit board are stacked in multiple stages.

Furthermore, in the case where the face of the electrode included in the electrode group with which the subject comes in contact constitutes a dent-shaped portion on an outer face of the body fat determining device, the subject can stably come in contact with the electrode along the dent to measure the impedance of the human body. Accordingly, it is possible to prevent the reproducibilies of the measurement from being deteriorated with a variation in the area of the electrode with which the subject comes in contact every time the body fat ratio is measured. Thus, the impedance of the human body can be measured stably.

Moreover, the body fat determining device can be formed to include a first face and a second face opposite to the first face. In such a case, all the electrodes included in the electrode group can be provided on the first face or the second face, the first current path forming electrode and the second current path forming electrode can be provided on the first face in the body fat determining device, the first measuring electrode and the second measuring electrode can be provided on the second face in the body fat determining device, the first current path forming electrode and the first measuring electrode can be provided on the first face, and the second current path forming electrode and the second measuring electrode can be provided on the second face.

Furthermore, in the case in which all or a part of operation switches provided in the body fat determining device for inputting individual data on the subject can also be used as all or a part of the electrodes included in the electrode group, the number of the members constituting the body fat determining device can be reduced and the body fat determining device can be small-sized.

Moreover, in the case where the electronic circuit board on which the electrode included in the electrode group is formed and circuit elements other than the electrode formed on the electronic circuit board are packaged by a mold, the circuit element and the like are collected into the mold. Consequently, the size and weight of the body fat determining device can be reduced.

Furthermore, in the case in which the body fat determining device is of a card type and the operation switch for inputting the individual data on the subject is formed on the first face of the body fat determining device of the card type, it is possible to obtain a portable body fat determining device which can easily be carried like a card. Thus, a body fat ratio can usually be measured easily.

Moreover, a printed board can be used as the electronic circuit board on which the electrode group is formed. In addition, a flexible printed circuit can also be used.

BRIEF DESCRIPTION OF THE DRAWINGS

FIG. 3 is a view showing a printed board on which an electrode is formed.

FIG. 4 is a block diagram showing the body fat determining device.

FIG. 5 is a view showing an example of the shape of the electrode and the like.

BEST MODE OF CARRYING OUT THE INVENTION

Figure 1:
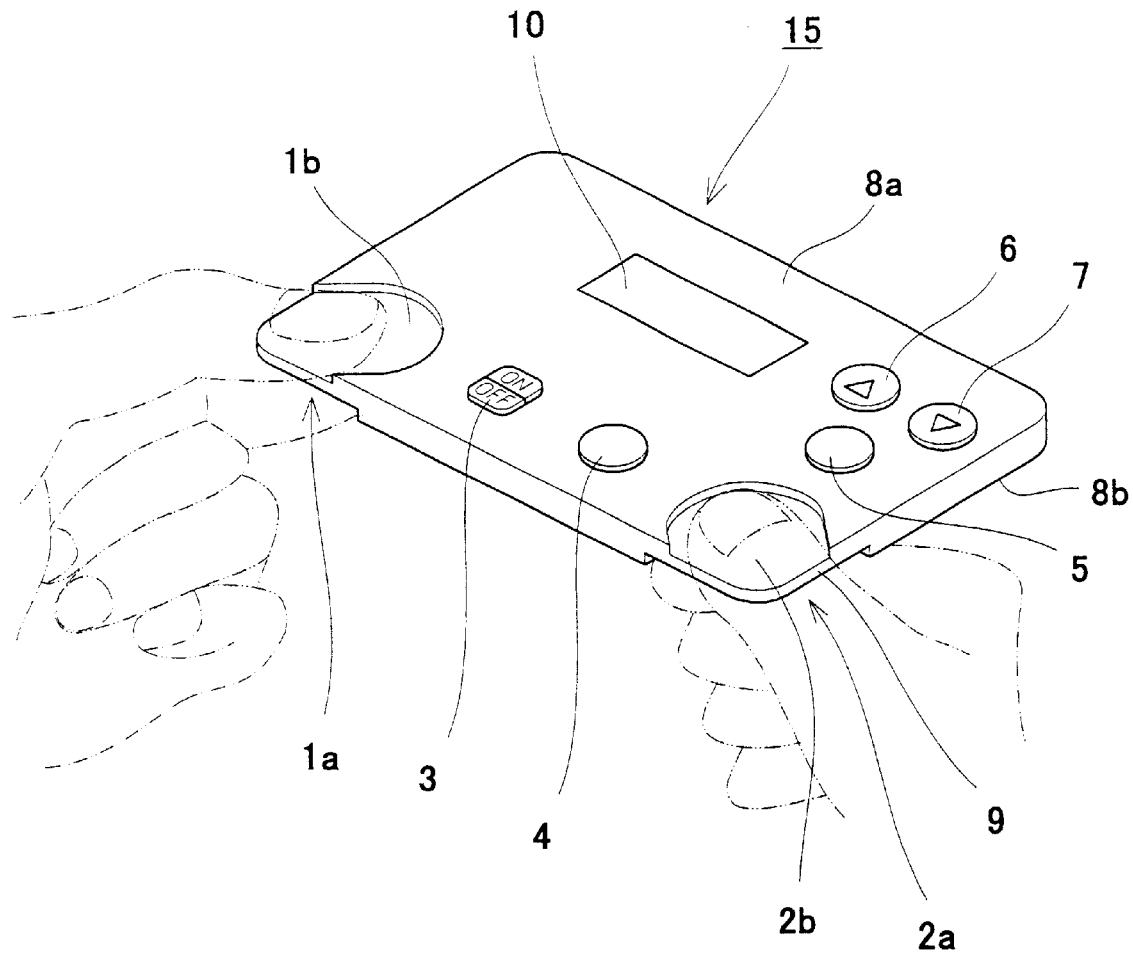
FIG. 1 is a perspective view showing a body fat determining device.
Figure 2A:
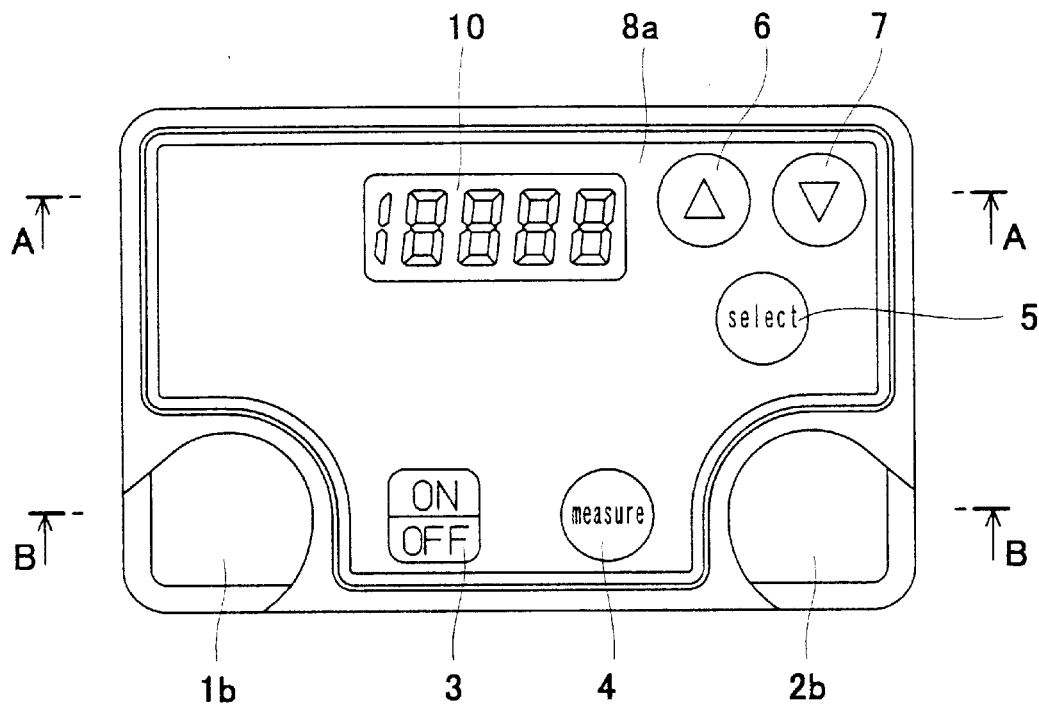
FIG. 2(a) is a top view showing the body fat determining device.
Figure 2B:
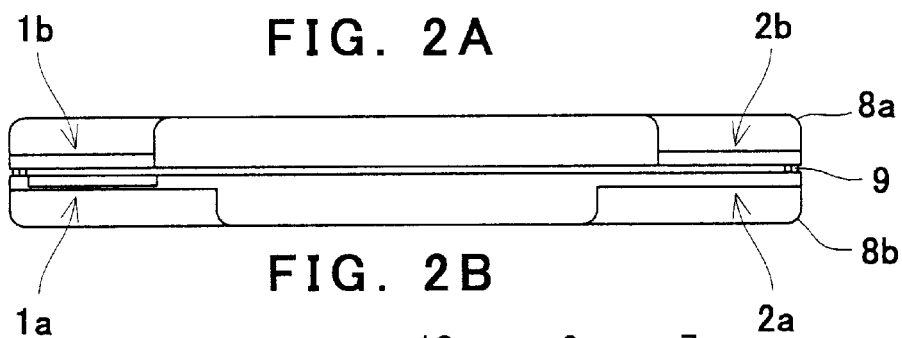
FIG. 2(b) is a front view showing the body fat determining device.
Figure 2C:
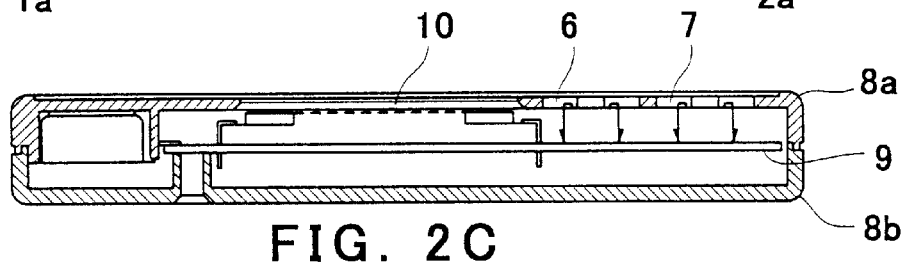
FIG. 2(c) is a sectional view taken along the line A—A in FIG. 2(a).
Figure 2D:
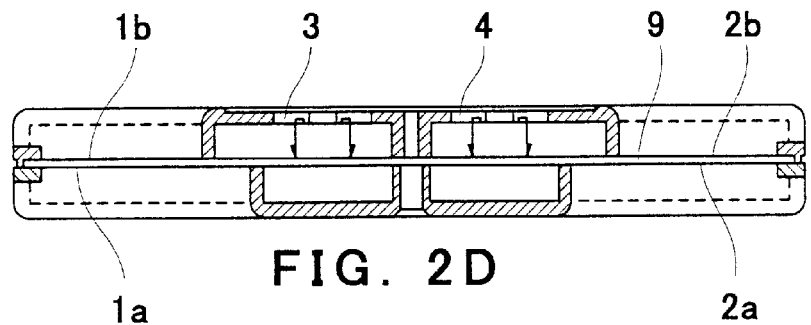
FIG. 2(d) is a sectional view taken along the line B—B in FIG. 2(a).

An embodiment of the present invention will be described with reference to FIGS. 1 to 7. FIG. 1 is a perspective view showing a body fat determining device 15 of a card type according to an embodiment of the present invention. FIG. 2(a) is a top view showing the body fat determining device 15, FIG. 2(b) is a front view showing the body fat determining device 15, FIG. 2(c) is a sectional view taken along the line A—A, and FIG. 2(d) is a sectional view taken along the line B—B.

The body fat determining device 15 is of a card type and has such a structure that a printed board 9 to be described below is incorporated between a body case 8a constituting the surface side of the body fat determining device 15 and a body case 8b constituting the back face side of the body fat determining device 15. As will be described below, various circuit elements necessary for functioning as the body fat determining device are mounted on the printed board 9.

An ON/OFF switch 3 is provided on the surface of the body fat determining device 15. The ON/OFF switch 3 is an operation switch for turning ON such that the body fat determining device 15 can be set in an operable state to measure a body fat ratio and for turning OFF to terminate the operation of the body fat determining device 15.

Moreover, a selection switch 5 for inputting the individual data on a subject which are necessary for calculating a body fat ratio, an increment key 6 and a decrement key 7 are provided on the surface of the body fat determining device 15.

The selection switch 5 is an operation switch for selecting the items of the individual data. The individual data include a height, a weight, an age, a sex and the like. By the operation of the selection switch 5, the items of the individual data to be input can be selected. The increment key 6 serves to increase the numerical value of the data when inputting the individual data, and the decrement key 7 serves to decrease the numerical value. By the combination of the operations of the selection switch 5, the increment key 6 and the decrement key 7, the individual data can be input.

Furthermore, a display section 10 for displaying the input individual data and the finally calculated body fat ratio is provided on the surface of the body fat determining device 15. By the display section 10, the input of the individual data can be confirmed and the body fat ratio can also be known as a result of measurement. In the body fat determining device 15, a liquid crystal display (LCD) is used for the display section 10.

Moreover, a measuring switch 4 for starting the measurement of an impedance of a human body is provided on the surface of the body fat determining device 15. In order to obtain the body fat ratio, it is necessary to measure the impedance of the human body as will be described below. By turning ON the measuring switch 4, each element for measuring the impedance of the human body which is not shown but is provided in the body cases 8a and 8b starts an operation thereof.

Furthermore, the body fat determining device 15 comprises an electrode group including four electrodes for obtaining the impedance of the human body required together with the individual data in order to find the body fat ratio. The electrode group includes a first current path forming electrode 1a and a second current path forming electrode 2a which serve to form a current path between two points of the body of the subject, and a first measuring electrode 1b and a second measuring electrode 2b which serve to measure a voltage between two points in the current path. In the body fat determining device 15, the first current path forming electrode 1a and the second current path forming electrode 2a are provided on the back face side of the body fat determining device 15, and the first measuring electrode 1b and the second measuring electrode 2b are provided on the surface side of the body fat determining device 15. In the body fat determining device 15, the first current path forming electrode 1a is positioned just on the back of the first measuring electrode 1b and the second current path forming electrode 2a is positioned just on the back of the second measuring electrode 2b.

In order to measure the impedance of the human body of the subject, the subject can press his (her) index finger of the left hand, his (her) thumb of the left hand, his (her) index finger of the right hand and his (her) thumb of the right hand in contact with the first current path forming electrode 1a, the first measuring electrode 1b, the second current path forming electrode 2a and the second measuring electrode 2b as shown in a dotted line of FIG. 1, respectively.

Then, the impedance of the human body of the subject through these electrodes is measured by well-known impedance measuring means which is not shown but is provided in the body cases 8a and 8b. More specifically, an element constituting a constant current source for outputting a constant current to form the current path, an element constituting a voltmeter for measuring the voltage and each element such as a CPU for calculating an impedance are provided in the body cases 8a and 8b.

As shown in FIG. 1 and FIG. 2(b), in the electrodes 1a, 1b, 2a and 2b, surfaces with which the subject comes in contact constitute dent-shaped portions for the body cases 8a and 8b. Consequently, the subject can cause his (her) finger to stably come in contact with the electrode along the dent. Accordingly, it is possible to prevent the reproducibility of measurement from being deteriorated with a variation in the area of the finger coming in contact with the electrode every time the body fat ratio is measured. Thus, the reproducibility of the measurement can be enhanced and the measurement of the impedance of the human body can be stabilized.

The electrodes 1a, 1b, 2a and 2b are formed on the printed board 9.

The printed board 9 is a printed wiring board formed of an epoxy resin plate or the like. The electrode on the printed board 9 is formed by scraping off a resist in a necessary portion of the printed board 9 where the electrode is to be formed and exposing a conductor in the printed board 9. Thus, if the electrode necessary for the measurement of the impedance of the human body is formed by using a conductor included in the printed board 9, the following advantages can be obtained. More specifically, it is not necessary to particularly provide only the electrode itself, and furthermore, it is not necessary to use a special support member for supporting the electrode, a wiring and the like. Consequently, it is also possible to reduce the size of the body fat determining device by decreasing the number of parts constituting the body fat determining device and to decrease a working man-hour for manufacturing the body fat determining device. Thus, the manufacturing cost of the body fat determining device can also be reduced. Moreover, a wiring for connecting the electrode to other circuit elements is not required. Consequently, troubles are not made by a disconnection or contact failure caused by providing the wiring. Consequently, the quality of the body fat determining device can be enhanced as a product.

Moreover, various circuit elements to be provided as the body fat determining device 15 are also mounted on the printed board 9. The electrodes 1a, 1b, 2a and 2b are connected to each element constituting the impedance measuring means through a circuit pattern formed on the printed board 9.

The printed board is used as an electronic circuit board for forming the electrode. Consequently, it is possible to reduce the size and cost of the body fat determining device.

An example of the printed board 9 is shown in FIG. 3. FIG. 3(a) is a plane view showing the printed board, and FIG. 3(b) is a view showing the printed board seen from a side. As shown in FIG. 3, a LCD constituting the display section 10 and an integrated circuit (IC) for controlling the operation of the body fat determining device 15 are mounted.

A part of specific elements mounted on the printed board 9 are shown in FIGS. 2(c) and 2(d). More specifically, the LCD 10, the increment key 6 and the decrement key 7 are mounted on the printed board 9 as shown in FIG. 2(c). Moreover, an ON/OFF switch 3 and a measuring switch 4 are mounted on the printed board 9 as shown in FIG. 2(d).

FIG. 4 is a block diagram illustrating the measurement of a body fat ratio in the body fat determining device 15. More specifically, a function key includes the selection key 5, the increment key 6, the decrement key 7 and the like. A storage device 21 stores individual data input through the operation of the function key, the measured value of the impedance of the human body obtained thorough the electrode group and the like as well as various operation expressions, coefficients and the like which are necessary for calculating the body fat ratio. The operation for calculating the body fat ratio based on the individual data, the operation expressions and the like stored in the storage device 21 is executed based on the operation of a central processing unit (CPU) 22. Moreover, after the power source of the body fat determining device 15 is turned ON, the data are input and output between each portion through an input/output device (I/O) 23 in the process of each data processing for calculating the body fat ratio.

Figure 5A:
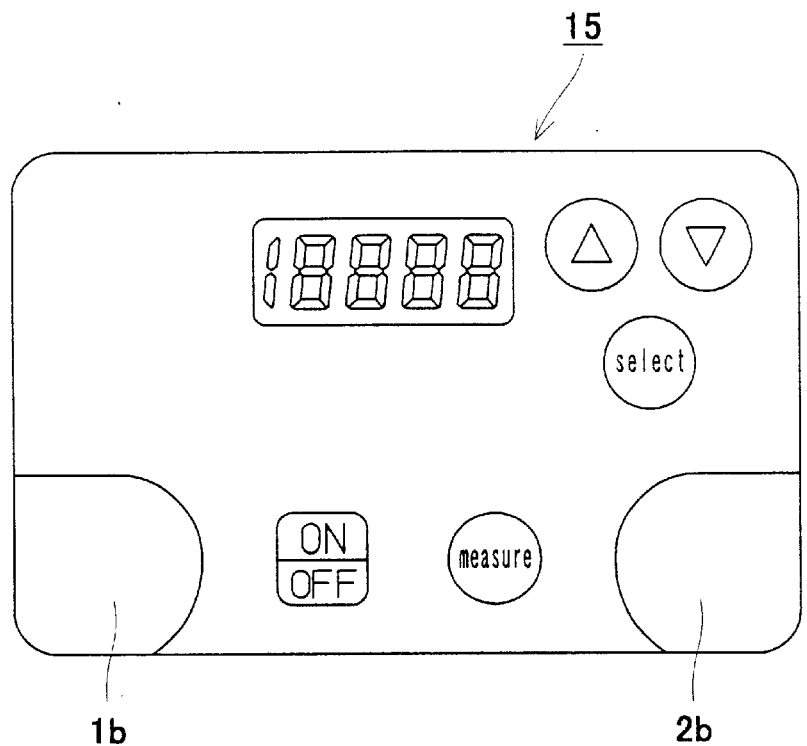
Figure 5B:
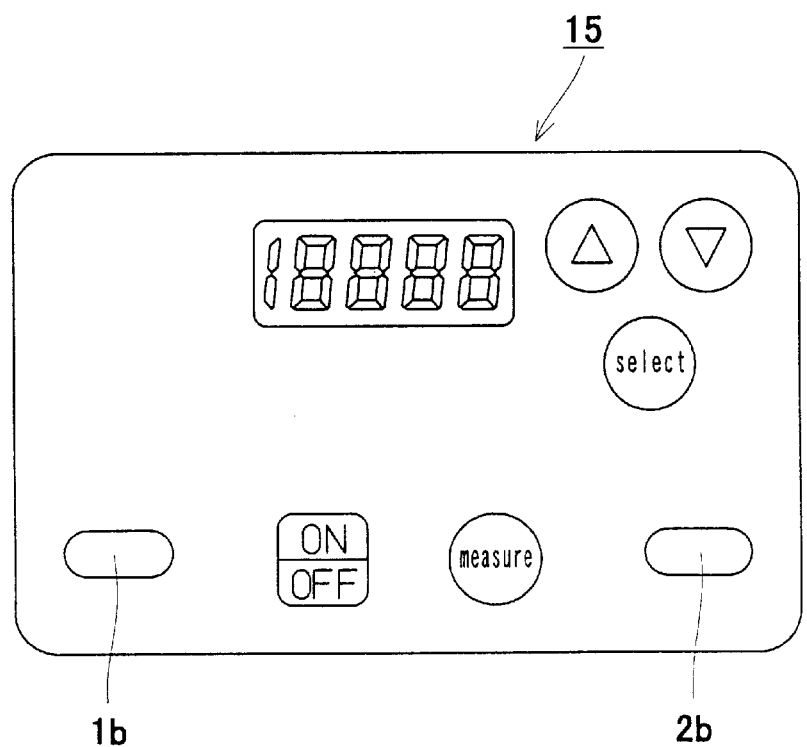

Furthermore, the portion in the body fat determining device 15 where the electrode is to be provided can also take the shapes of the electrodes 1b and 2b shown in FIG. 5 in addition to the shapes shown in FIGS. 1 and 2 and the like. In other words, the electrode may be formed as shown in FIG. 5(b) as well as FIG. 5(a). FIG. 5(b) shows an example in which the electrode is not formed in a position including the end of the body fat determining device 15 as shown in FIGS. 1 and 5(a) but in other positions. Also in the case where the electrode is to be formed in the position shown in FIG. 5(b), the surface of each electrode with which the subject comes in contact can be constituted to be dent-shaped for the body cases 8a and 8b.

Moreover, while the first current path forming electrode 1a and the second current path forming electrode 2a are provided on the back face side of the body fat determining device 15 and the first measuring electrode 1b and the second measuring electrode 2b are provided on the surface side of the body fat determining device 15, the electrodes 1a and 2a may be provided on the surface side of the body fat determining device 15 and the electrodes 1b and 2b may be provided on the back face side. Furthermore, the electrodes 1a and 1b may be provided on the surface side and the electrodes 2a and 2b may be provided on the back face side.

Furthermore, all the electrodes 1a, 1b, 2a and 2b may be provided on the surface side or back face side of the body fat determining device 15. Also in this case, the surface of each electrode with which the subject comes in contact can be constituted to be dent-shaped for the body cases 8a and 8b.

Moreover, the operating switch such as the increment key 6 or the decrement key 7 and the electrode may also be shared. For example, if the key 6 and the like can be selected for functioning to input the individual data or functioning to measure the impedance of the human body through the operation of the measuring switch 4, the increment key 6 and the like can be caused to function as both of the operation switch for inputting the individual data and the electrode for measuring the impedance of the human body.

Furthermore, the printed board 9 on which the electrode is to be formed may be provided separately from other boards on which elements other than the electrode are mounted and may be connected to the other boards through a flat connector for the printed board or the like. Thus, the printed board 9 on which the electrode is to be formed can also be removed from the body fat determining device 15.

Figure 6:
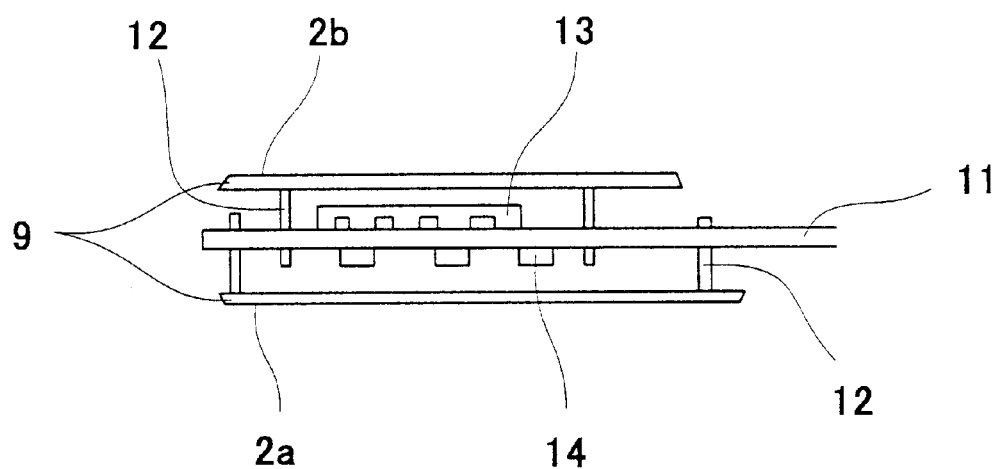
FIG. 6 is a view showing an example in which an electronic circuit board is stacked in multiple stages.

As shown in FIG. 6, moreover, the printed board 9 for forming the electrode and a board 11 acting as another printed board for mounting circuit elements other than the electrode may be provided, and the printed board 9 and the printed board 11 may be stacked in multiple stages in the vertical direction in the body cases 8a and 8b of the body fat determining device. With such a structure having a multi-stage stack, elements such as an IC 13, a chip resistor 14 and the like which are to be mounted on the printed board 11 can be provided in a space between the printed board 9 and the printed board 11. By utilizing such a space, it is possible to suppress the transverse extension of the space for mounting the elements (the horizontal and vertical directions of a paper). Consequently, the transverse extension of the body fat determining device can also be suppressed to reduce a size. Elements other than the electrode may be mounted on the printed board 9.

Thus, in the case where the printed board 9 and the printed board 11 on which other elements are to be mounted are stacked in the vertical direction, a part of the electrodes 2a, 2b and the like of the board 9 and the necessary portion of the board 11 are short-circuited by a bar-shaped conductor 12. Thus, also in the case where the printed board 9 on which the electrode is to be formed and the board on which other elements are to be mounted are stacked in the vertical direction, all the electrodes necessary for measuring the impedance of the human body may be formed on one of faces of the printed board 9.

Figure 7:
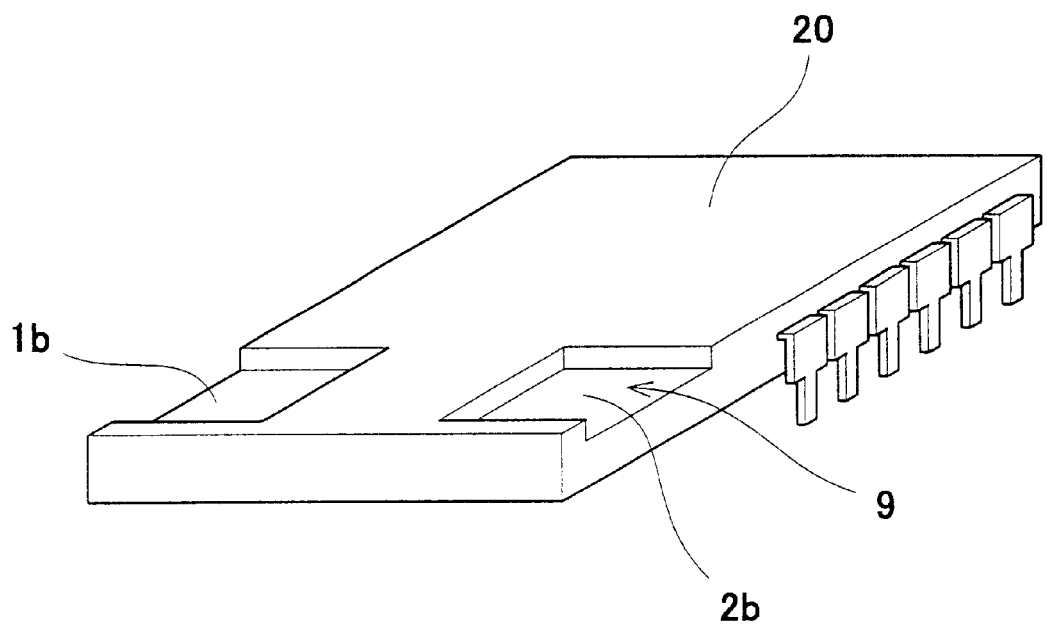
FIG. 7 is a view showing an example in which packaging is carried out by a mold.

Moreover, the printed board 9 on which the electrode is to be formed may be packaged by a mold 20 as shown in FIG. 7. FIG. 7 is a perspective view showing the mold 20. The printed board 9 on which the electrodes 1b and 2b are formed as shown in FIG. 7 is packaged by the mold 20 together with elements other than an electrode provided on the mold 20. When the packaging is carried out by the mold 20, the printed board 9 on which the electrode is to be formed and the elements other than the electrode can be covered and collected. Therefore, the size and weight of the body fat determining device can be reduced.

While the electrode necessary for measuring the impedance of the human body has been formed on the printed board in the above description, the electrode may be-formed on a flexible printed circuit (FPC) which is one of electronic circuit boards. In the case in which the electrode is formed in the FPC, a work for manufacturing the body fat determining device or the like can easily be carried out because the FPC is flexible.

Furthermore, also in the case in which the electrode is to be formed on the flexible printed circuit, the electrode can be formed by scraping off an insulating material portion on a surface thereof to expose a conductor portion.

INDUSTRIAL APPLICABILITY

As described above, the body fat determining device according to the present invention has such a structure that an electrode group for measuring an impedance of a human body is formed on an electronic circuit board. Consequently, the number of parts constituting the body fat determining device can be decreased to reduce the size of the body fat determining device and a working man-hour for manufacture can be decreased. Moreover, the manufacturing cost of the body fat determining device can also be reduced.

Furthermore, the electronic circuit board on which the electrode group is to be formed serves to mount circuit elements other than the electrode group which constitute the body fat determining device. Consequently, the size of the body fat determining device can be reduced still more. By sharing various operation switches provided in the body fat determining device and each electrode included in the electrode group, moreover, the size of the body fat determining device can be reduced still more.

What is claimed is:

1. A body fat determining device comprising:
    an electrode group including a first current path forming electrode and a second current path forming electrode for forming a current path together with the first current path forming electrode, and a first measuring electrode and a second measuring electrode for measuring an impedance together with the first measuring electrode; and
    an electronic circuit board on which a circuit element is provided and a body case,
    wherein the electrode included in the electrode group is formed on the electronic circuit board, and
    the electrode group is formed with a face with which a subject comes in contact exposed to an outside of the body case in such a manner that the subject can come in contact to measure his (her) impedance, wherein the face of the electrode included in the electrode group with which the subject comes in contact is exposed to the outside of the body case by forming a dent-shaped portion on an outer face of the body fat determining device.

2. The body fat determining device according to claim 1, wherein the electronic circuit board on which the electrode is formed is provided with a circuit element constituting the body fat determining device.

3. The body fat determining device according to claim 1, wherein the electronic circuit board on which the electrode is formed and another electronic circuit board on which circuit elements other than the electrode formed on the electronic circuit board are provided have a multi-stage structure.

4. The body fat determining device according to any of claims 1 to 3, wherein the body fat determining device is formed to include a first face and a second face opposite to the first face, and
    all the electrodes included in the electrode group are provided on the first face or the second face.

5. The body fat determining device according to any of claims 1 to 3, wherein the body fat determining device is formed to include a first face and a second face opposite to the first face,
    the first current path forming electrode and the second current path forming electrode are provided on the first face in the body fat determining device, and
    the first measuring electrode and the second measuring electrode are provided on the second face in the body fat determining device.

6. The body fat determining device according to any of claims 1 to 3, wherein the body fat determining device is formed to include a first face and a second face opposite to the first face, the first current path forming electrode and the first measuring electrode are provided on the first face, and the second current path forming electrode and the second measuring electrode are provided on the second face.

7. The body fat determining device according to any of claims 1 to 3, wherein all or a part of operation switches provided in the body fat determining device for inputting individual data on the subject are also used as all or a part of the electrodes included in the electrode group.

8. The body fat determining device according to any of claims 1 to 3, wherein the electronic circuit board on which the electrode is formed and circuit elements other than the electrode formed on the electronic circuit board are packaged by a mold.

9. The body fat determining device according to any of claims 1 to 3, wherein the body fat determining device is of a card type and the operation switch for inputting the individual data on the subject is formed on the first face of the body fat determining device of the card type.

10. The body fat determining device according to any of claims 1 to 3, wherein the electronic circuit board on which the electrode is formed is a printed board.

11. The body fat determining device according to any of claims 1 to 3, wherein the electronic circuit board on which the electrode is formed is a flexible printed circuit (FPC).

* * * * *